(12) United States Patent
Agnew (10) Patent No.: US 9,675,438 B2
(45) Date of Patent: Jun. 13, 2017

(54) DOME-SHAPED VASCULAR FILTER

(71) Applicant: Cook Medical Technologies LLC, Bloomington, IN (US)

(72) Inventor: Charles W. Agnew, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 197 days.

(21) Appl. No.: 13/901,132

(22) Filed: May 23, 2013

(65) Prior Publication Data

US 2013/0253573 A1 Sep. 26, 2013

Related U.S. Application Data

(63) Continuation of application No. PCT/US2011/060923, filed on Nov. 16, 2011.

(60) Provisional application No. 61/416,798, filed on Nov. 24, 2010.

(51) Int. Cl.
*A61F 2/01* (2006.01)

(52) U.S. Cl.
CPC .......... *A61F 2/01* (2013.01); *A61F 2002/016* (2013.01); *A61F 2230/005* (2013.01); *A61F 2230/008* (2013.01)

(58) Field of Classification Search
CPC .................. A61F 2/01; A61F 2230/008; A61F 2230/005; A61F 2230/016; A61F 2002/016
See application file for complete search history.

(56) References Cited

U.S. PATENT DOCUMENTS

| | | | |
|---|---|---|---|
| 5,059,205 A | 10/1991 | El-Nounou et al. | |
| 5,102,415 A * | 4/1992 | Guenther et al. | 606/159 |
| 5,800,457 A * | 9/1998 | Gelbfish | 606/200 |
| 6,013,093 A * | 1/2000 | Nott et al. | 606/200 |
| 6,217,600 B1 | 4/2001 | Dimatteo | |
| 6,436,120 B1 | 8/2002 | Meglin | |
| 6,482,222 B1 | 11/2002 | Bruckheimer et al. | |
| 6,506,205 B2 | 1/2003 | Goldberg et al. | |
| 6,551,342 B1 | 4/2003 | Shen et al. | |
| 6,726,621 B2 | 4/2004 | Suon et al. | |
| 2005/0038470 A1* | 2/2005 | van der Burg et al. | 606/213 |
| 2005/0080338 A1* | 4/2005 | Sirimanne et al. | 600/431 |
| 2005/0165441 A1 | 7/2005 | McGuckin et al. | |
| 2006/0287701 A1* | 12/2006 | Pal | A61F 2/013 623/1.11 |
| 2007/0088381 A1 | 4/2007 | McGuckin et al. | |
| 2009/0005803 A1 | 1/2009 | Batiste | |

FOREIGN PATENT DOCUMENTS

WO  WO 03/092537  11/2013

* cited by examiner

*Primary Examiner* — Anh Dang
(74) *Attorney, Agent, or Firm* — Christopher Brown (57) ABSTRACT

There is disclosed embodiments of a vascular filter having, among other things, a plurality of discrete segments, each having two or more loops and an extension. The loops of each segment can be connected to form a dome or conical shaped end with an unblocked central opening. Prongs and beads may be provided to enhance visualization and anchoring in a vessel. Methods for inserting and moving or removing the filter from the vessel are also disclosed.

20 Claims, 6 Drawing Sheets

DOME-SHAPED VASCULAR FILTER

CROSS-REFERENCE TO RELATED APPLICATIONS

The present application is a continuation of International Application No. PCT/US2011/060923, filed Nov. 16, 2011, pending which claims the benefit under 35 USC §119(e) of U.S. Provisional Patent Application Ser. No. 61/416,798, filed Nov. 24, 2010, each of which is hereby incorporated by reference herein.

The present disclosure relates to medical devices. More particularly, the disclosure relates to an easily placeable and removable filter for clots or other obstructions that can be percutaneously placed in and removed from vessels or other locations in a patient.

BACKGROUND

Filtering devices that are percutaneously placed in blood vessels have been available for many years. A need for filtering devices can arise, for example, in trauma patients, orthopedic surgery patients, neurosurgery patients, or in patients having medical conditions requiring bed rest or non-movement. During such medical conditions, the need for filtering devices arises where there is a likelihood of thrombosis in the peripheral vasculature of patients wherein clot material, stenosis material or other particles break away from the vessel wall, risking downstream blockage of the vessel or other damage. For example, depending on the size, such break-away material could pose a serious risk of pulmonary embolism, i.e. wherein blood clots migrate from the peripheral vasculature through the heart and into the lungs.

A filtering device can be deployed in the vasculature of a patient when, for example, anticoagulant therapy is contraindicated or has failed. Typically, filtering devices are permanent implants, each of which remains implanted in the patient for life, even though the condition or medical problem that required the device has passed. In more recent years, filters have been used or considered in preoperative patients and in patients predisposed to thrombosis which places the patient at risk for embolism.

The benefits of a vascular filter have been well established, but improvements may be made. For example, filters generally have not been considered removable from a patient due to the likelihood of endotheliosis of the filter or fibrous reaction matter adherent to the endothelium during treatment. After deployment of a filter in a patient, proliferating intimal cells begin to accumulate around the filter struts which contact the wall of the vessel. After a length of time, such ingrowth may prevent removal of the filter, or may risk significant trauma during removal through a layer of endothelium, requiring the filter to remain in the patient. Where removal has been considered, filters have been provided with a central hook for gripping in order to pull the filter during removal. Such hooks can be difficult to find or latch onto, and may be covered by cellular growth. They further provide the opportunity only to pull the filter in one direction or to remove it in only one direction. As a result, there has been a need for an effective filter that can be removed after the underlying medical condition has passed.

Another difficulty with conventional filters is that they may become off-centered or tilted with respect to the hub of the filter and the longitudinal axis of the vessel in which it has been inserted. As a result, the filter including the hub and the retrieval hook engage the vessel wall along their lengths and potentially become endothelialized therein. In the event of this occurrence, there is a greater likelihood of endotheliosis of the filter to the blood vessel along a substantial length of the filter wire. As a result, the filter becomes a permanent implant in a shorter time period than otherwise. Moreover, a tilted filter may not provide protection against traveling emboli across as much of the cross-sectional area of the vessel as a properly-oriented filter would.

It has been a challenge to design a vascular filter with features that permit easy insertion and retrieval of the filter while maintaining the effectiveness of the filter.

SUMMARY

Among other things, there is disclosed a vascular filter system that includes a vascular filter made of a plurality of segments. In particular embodiments, each segment includes at least a first loop, a second loop, and a curvilinear extension, with the second loop fixed to the first loop and the extension, and each first loop is connected to one or more adjacent first loops so that the first loops define an opening between them. Each of the second loops may be connected to one or more adjacent second loops. An expandable member is provided in some embodiments that is extendable at least through that opening, with the expandable member having a first contracted state in which it can be moved through the opening and/or one or more of the loops, and a second expanded state in which it cannot be moved through the opening and/or one or more of the loops. Expanding the expandable member within the filter allows the expandable member to engage the filter to pull or buttress the filter in a blood vessel.

In particular embodiments, a tubular member with a lumen can be provided that is adapted to be inserted into the vascular system, with the expandable member extendable from it. The lumen is adapted to accommodate the filter being moved into it from a position in a blood vessel. Each of the segments may be substantially identical. Some embodiments have at least a first of the first loops connected to a second of the first loops by twisting respective portions of them together, and others have at least a first of the first loops connected to a second of the first loops by a holding piece (e.g. an echogenic bead) that holds respective portions of them with respect to each other. A plurality of visualizable beads can be provided so that each first loop is linked to its adjacent first loops by one of such beads, and such beads can lie substantially in a single plane that is at least approximately perpendicular to a central longitudinal axis of the filter. Particular embodiments include first and second prongs placed generally at opposite ends of the respective extension of each segment. In such cases, the filter can be configured so that on placement in a vessel at most a portion of the extensions and a portion of the first and second prongs contact the vessel.

Also disclosed is a vascular filter system that includes a vascular filter having a plurality of segments joined together. Each segment includes a first loop, a second loop fixed to the first loop, and an extension fixed to the second loop and extending generally away from the first loop. The first loop of each segment is joined to at least one other first loop, and the second loop of each segment is joined to at least one other second loop. The first loops when joined together bound a central longitudinal opening that is surrounded by the first loops, and the extensions are curved so that their respective internally-facing portions are concave.

Along with those examples, other features are contemplated. For example, at least one of the segments can include a first prong located at or adjacent to the point where the extension and second loop of a segment are fixed together, and a second prong may be located on the extension distal from the second loop. In particular, the filter is configured so that when properly placed in a vessel only a portion of the extension and a portion of the prongs contact the vessel. At least one of the segments may include a first bead contacting the first prong and the extension and second loop, and a second bead contacting the second prong and the extension, with the first and second beads acting as a limit on the distance the first and second prongs can be inserted into tissue. Such first and second prongs can be substantially parallel to each other, and/or the second prong can form an acute angle with respect to the extension. In some embodiments, the filter includes at least one bead contacting two adjacent ones of the first loops, and the beads can be echogenic. The filter in other embodiments includes a series of beads each contacting two adjacent ones of the first loops, with the series of beads being generally in a plane. Examples of filters can also include at least one echogenic bead on a portion of one of the first loops adjacent to the central longitudinal opening.

Along with such structure an expandable or inflatable member (e.g. a balloon catheter) can be provided that has a non-inflated state and an inflated state. The non-inflated state is of a size that allows the inflatable member to pass through one or more of the central longitudinal opening and the loops, and the inflated state is of a size that does not allow the inflatable member to pass through that one or more of the central longitudinal opening and the loops. Further, a catheter or other tube can be provided through which the inflatable member extends and from which the inflatable member is moved through the filter. The tube may be sized and configured to permit placing the inflatable member and the filter into the tube so as to remove the filter from the vessel.

Particular embodiments of a filter for positioning within the fluid passageway of a blood vessel in a human body include a downstream filtering portion and an upstream holding portion. The filtering portion has a first set of a plurality of wire loops connected together, each such wire loop of the first set connected to at least one other wire loop of the first set. It also has a second set of a plurality of wire loops connected together, each such wire loop of the second set connected to at least one other wire loop of the second set. Each such wire loop of the second set is connected to at least one wire loop of the first set. The holding portion has a plurality of curved wire portions, each of which is connected to and extending from at least one wire loop of the second set and extending away from the wire loops of the first set. The first set of wire loops are connected together so that they define an opening surrounded by the first set of wire loops.

In a particular embodiment shown herein, a filter includes a series of discrete sections or segments of wire (e.g. of a superelastic material such as nitinol). Each wire is twisted to form a proximal (apical) loop and second larger loop located distal of the first loop. One end of the wire terminates about the distal end of the second loop to form a proximal barb while the second end of the wire extends distally to form a leg or extension of the filter, terminating in a distal prong or barb. A series of these sections (the number depending on the size of the filter) are joined to create the filter. The sections could be joined by intertwining the wire loops with loops of adjacent sections, or by sliding or forming beads over adjacent wires, placing cannulae or wraps over adjacent wires and crimping, or otherwise affixing adjacent wires in the desired position. Ideally, such beads, crimps or other attaching structures would include a radiopaque material so as to become markers for radiographic imaging, as well being sized or configured to function as echogenic markers for allowing placement under external ultrasound or intravascular ultrasound (IVUS). These beads can be placed anywhere along the wires to serve as markers, including adjacent the distal prongs or barbs where they also can function to limit penetration of the prong into the vascular wall. Because of the large number of prongs in particular embodiments (e.g. two for each section or segment, or 12 for an embodiment having six sections), the filter can be made of a thinner diameter nitinol wire (perhaps 0.008" to 0.010") as there is less reliance on the radial force of the barbed legs against the vessel wall to prevent migration. The additional proximal prongs also will help prevent tilting of the device upon implantation. Such thin wire helps lower the profile of the device and allow it to be more readily resheathed, even with prongs being angled in a proximal direction.

Manufacture of the filter can use a dome-shaped mandrel over which the nitinol wire sections would be assembled and heat set into the desired configuration. Alternatively, a filter can be laser-cut from a nitinol cannula in which the proximal (latticed) end is heat set into a closed configuration (or drawn in a secured with suture, wire, connectors, etc.). The laser-cut prongs or barbs could be heat set or cold worked to move them out of a plane of their respective leg or other parts of the filter.

Methods of delivering the filter can include being pushed out of a catheter, sheath or similar vascular delivery device using a pusher member, so that the filter expands into contact with a vessel, or being mounted over an inner member such as a malecot catheter or similar device that could act as a holder or retainer to better control positioning and deployment (e.g. by expansion) of the filter. Methods of retrieving a filter are also disclosed. For example, a tapered, expandable device, such as a small diameter malecot device, basket, balloon, or similar device is pushed through any space or opening between the wires at the proximal end of the filter (e.g. a space within a particular loop, or an opening bounded by apical loops). Once through the filter, the device is expanded to provide a shoulder, which urges the filter proximally when the device is pulled until the filter dislodges from the wall. The filter could be pulled into the sheath by collapsing the expandable retrieval means as the filter is drawn inside. Other devices (e.g. a hook or similar device) could be used instead of an expandable device to ensnare the wires of the lattice to pull the filter into a sheath. If the wires comprising the filter are sufficiently flexible, the retrieval device could be inserted from the opposite (distal) direction to evert the filter and collapse it into a sheath.

As indicated above, some of the clinical issues associated with intravascular filters include migration, tilting, barb penetration of the vessel wall, and ease of placement and retrieval. The present disclosure seeks to address these by having a hubless, dome-shaped filter with a lattice-like structure extending across the lumen of the vessel, the lattice structure having a series of openings through which a retrieval device can be traversed to engage the filter and pull it into a resheathing device. The lattice is configured such that a retrieval device does not have to penetrate through any particular opening in order to engage and retrieve the filter, thus making retrieval easier for the clinician than filters which require engaging a specific target structure, such as a retrieval hook.

DESCRIPTION OF THE ILLUSTRATED EMBODIMENTS

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated embodiments, and such further applications of the principles of the disclosure as illustrated therein being contemplated as would normally occur to one skilled in the art to which the disclosure relates.

Referring now generally to the drawings, there is shown an embodiment of a filter 20 for use in the circulatory system to contain travel of emboli (e.g. clotted blood, stenosed material or other potential obstructions). As will be discussed further below, in certain embodiments filter 20 is inserted into and at least temporarily fixed within a vessel (e.g. vein or artery) so that blood flow is directed through it. Emboli carried along by the flow are caught and held by filter 20, so that they do not move into organs or other vasculature and present a danger to the patient. At such time as the potential for emboli is reduced or eliminated, filter 20 can be removed easily from its location in the vessel.

Figure 1:
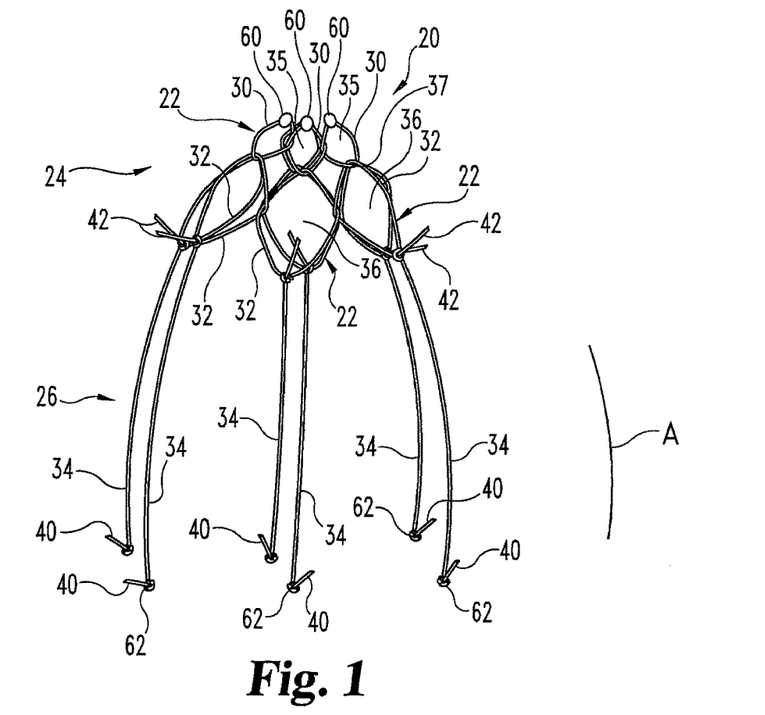
FIG. 1 is a perspective view of an embodiment of a vascular filter.
Figure 2:
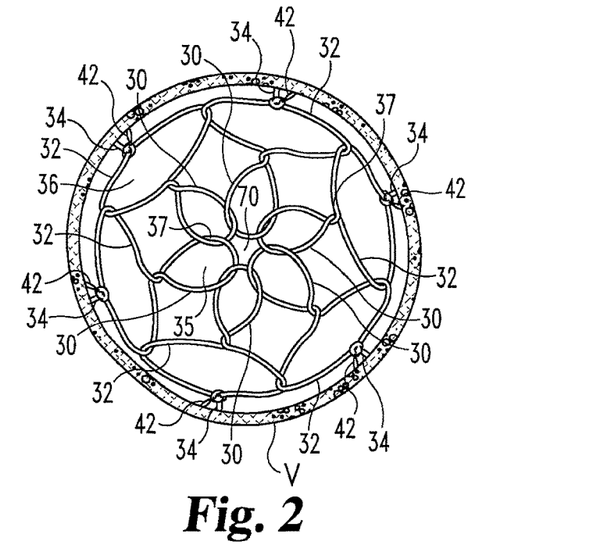
FIG. 2 is an end view of an embodiment generally like the embodiment of FIG. 1.

In the embodiment of FIG. 1, filter 20 includes a series of joined segments or sections 22 forming a domed or conical portion 24 for relative downstream or proximal placement and a portion 26 for relative upstream placement. While portion 24 is domed or conical in this embodiment, so as generally to direct emboli to the interior or center of filter 20, it will be understood that other shapes of portion 24 may be formed so as to allow blood flow while catching and holding emboli. Generally speaking, each segment 22 of this embodiment includes a plurality of loops (e.g. loops 30, 32) connected to or monolithic with a leg or extension 34. The illustrated embodiment shows a filter 20 including six segments 22, and thus six extensions 34. However, it will be understood that other embodiments can include a larger number (e.g. 7, 8, 9, 10 or more) or a smaller number (e.g. 4 or 5) of segments and extensions. The number of segments 22 depends on a number of factors, such as the size of the vessel or location at which filter 20 is to be placed, the size or thickness of the materials used to make segments 22, and the desired size of the loops or their openings in the segments. Use of six segments 22, as shown in the embodiment of FIGS. 1-2, is believed to provide an optimum size of filter 22 for use in a number of vascular locations and to exhibit features and advantages discussed below.

Figure 3:
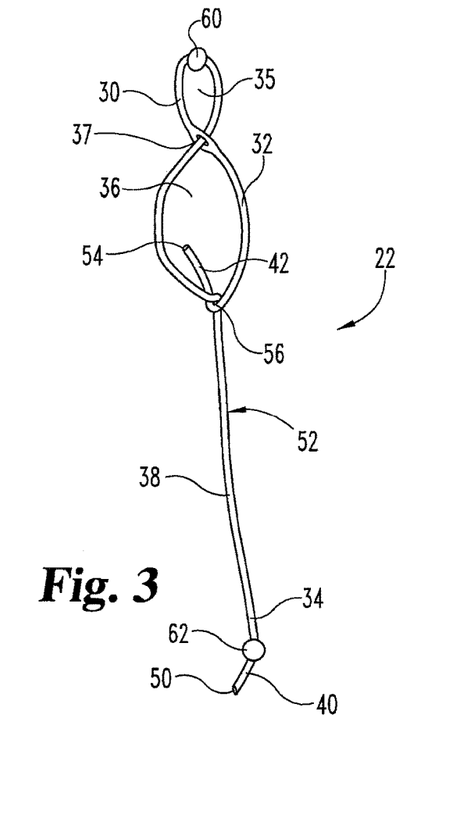
FIG. 3 is a side view of a portion or segment in an embodiment generally like the embodiment of FIG. 1.
Figure 3A:
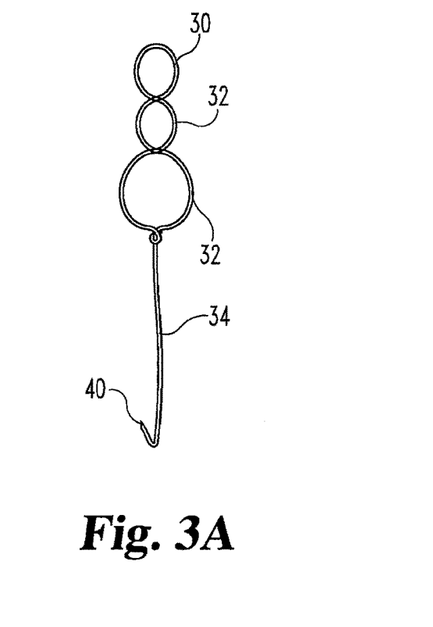
FIG. 3A is a side view of an alternative embodiment of a portion or segment of a vascular filter.

The example of segment 22 shown includes two loops 30 and 32 of solid material. Loops 30 and 32 are shown as elliptical (e.g. circular or oval) in this embodiment, each having respective openings 35, 36, with a joining point or location 37 situated along a line joining the centers of loops 30, 32. An extension 34 is joined to loop 32 and extends generally away from or opposite loop 30. Loop 30 is smaller in area (and in circumference) than loop 32 in this embodiment, so that when segments 22 are joined together (as discussed below) the individual loops 30 tend toward each other to form a general cone or dome shape. These shapes and such relative location of joining are believed to be advantageous in terms of ease of manufacture, sturdiness, and centralization of forces so as to limit or eliminate tilting or shifting in vivo, and to maximize area covered by an amount of wire or other material in loops 30, 32. In other embodiments, loops 30 and 32 may be otherwise shaped, and/or have a joining point 37 that is laterally offset with respect to one or both of the centers of loops 30, 32. In other embodiments (e.g. FIG. 3A), a segment 22 could include three or more loops 30, 32, 32'. Additional loop(s) can provide for a longer and/or slimmer filter 20, which may be useful for smaller-diameter vessels, or for locations with risks of more frequent or larger embolisms.

Each extension 34 is attached to the distal-most or upstream-most loop (loop 32 in FIG. 1, or loop 32' in FIG. 3A) of its respective segment 22, and extends in a distal or upstream direction. In the illustrated embodiment, extension 34 is a finger or leg having a length approximately that of the length of portion 24 or greater. That relatively long length is believed to be advantageous in maintaining and removing of filter 20 from the body when appropriate, at least in terms of the flexibility and stability they would provide. Extension 34 is curved in this embodiment so that it is externally convex as viewed from the side, that is, the edge of extension 34 that faces away from the central longitudinal axis of filter 20 is convex along its length, and the edge of extension 34 facing inwardly toward the central longitudinal axis of filter 20 is concave, as it runs from loop 32 to its proximal end, as indicated in FIG. 1 by arc A. In other embodiments, extension 34 may extend substantially linearly from loop 32 (or loop 32'), so that a series of extensions 34 of several segments 22 lie at least substantially along a portion of a cone.

These and other configurations of extensions 34 are believed to be advantageous as they enable contact of the inside of a blood vessel with a relatively small portion of each of extensions 34. Extensions 34 can act like leaf springs, so that portions of extensions 34 exert force against the inside of the vessel and hold filter 20 in place. Accordingly, the amount of extensions 34 that will be covered by growing endothelial cells within the vessel as filter 20 is reduced. In the curved embodiment, for example, the medial outermost external surface 38 of an extension 34 abuts the vessel, while portions that are more proximal or more distal of that surface have some separation from the vessel wall. Only the medial portion of extension 34 is likely to have endothelium grown on or over it within the vessel, while other portions are likely to have little or no tissue growth on or around them. The smoothly curved nature of the portion of the illustrated embodiment of extension 34 that contacts the vessel further helps minimize or eliminate damage to the inside of the vessel when filter 32 is removed.

The illustrated embodiment of segments 22 further includes multiple prongs 40, 42 that are separated from each other longitudinally. In a particular embodiment, one prong 40 is at or adjacent the upstream end of extension 34 (separated from portion 24 of filter 20), and one prong 42 is at or adjacent the link or connection point between extension 34 and loop 32. Prong 40 extends from extension 34 in one embodiment so that an acute angle is formed at the junction of prong 40 and extension 34. Prong 42 in this embodiment is approximately parallel to prong 40, and may be substantially perpendicular to loop 32 and/or extension 34, or may form an acute or slightly obtuse angle with loop 32 and/or extension 34. Prongs 40, 42 may be sharpened at their respective tips and/or form a barb, so that at least a portion enters the vessel or tissue wall when filter 20 is placed. Even if prongs 40, 42 are blunt, their small surface area against or proximate the vessel wall results in significant pressure between them and the inside of the vessel or tissue wall to maintain filter 20 in place. That small area also permits a limited opportunity for endothelial growth over prongs 40, 42, and during removal prongs 40, 42 may more easily be withdrawn from endothelial growth, e.g. substantially along a length or longitudinal axis of prongs 40, 42. Prongs 40, 42 are separated longitudinally by a significant distance in this embodiment, e.g. approximately the length of extension 34. Although two prongs 40, 42 are shown in this embodiment of segment 22, it will be understood that a single prong (e.g. prong 40) could be included, or more than two prongs could be placed on a segment 22. In other embodiments of filter 20, no prongs may be present.

Segment 22, as seen in the illustrated embodiment, may be made of a single strand of thin wire, of such materials as Nitinol or other superelastic material(s), combinations of such superelastic materials with other compatible materials, or other flexible and sturdy material. Superelastic materials such as Nitinol are believed to provide flexibility in a thin wire that will allow the compression and expansion of filter 20 with little or no damage to the vessel, as further noted below. In particular embodiments, the diameter of a cylindrical Nitinol wire could be approximately 0.008 to 0.010 inches. Such a diameter is thinner than is used in existing filters, so that filter 20 can be more flexible and use less material.

For example, using such a strand of thin wire, prong 40 is at or forms one end 50 of the wire. A bend is made in the body of the wire toward end 50, forming the junction between prong 40 and the rest of extension 34. A smooth curve is made in the body 52 of the wire to form extension 34. A loop is formed in body 52 of the wire so that the other end 54 of the wire crosses over body 52. That crossing point 56 is the connecting point or junction between extension 34 and loop 32, and end 54 of the wire that crosses over is twisted around body 52 to form prong 42. The loop initially formed in body 52 of the wire is twisted in the middle (e.g. three-fifths to two-thirds of the way from prong 42 to the other side of the initial loop), making the initial loop into two separate loops 30 and 32 connected (e.g. twisted or affixed) at location 37, with loop 30 being smaller than loop 32. Segment 22 in such an embodiment is thus a single length of thin wire bent, looped and twisted into loops 30, 32, extension 34, and prongs 40, 42.

Figure 6:
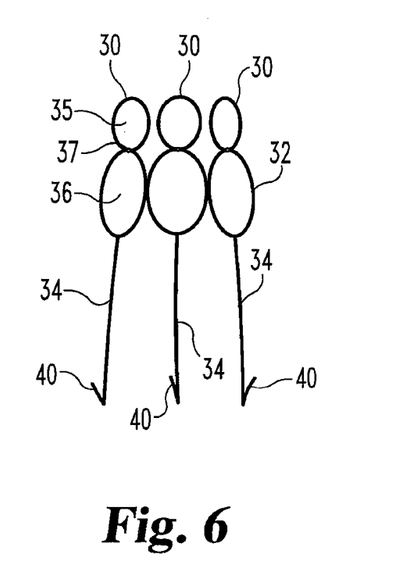
FIG. 6 is a side view of an embodiment of several portions like the portions shown in FIG. 4, partially connected together.
Figure 7:
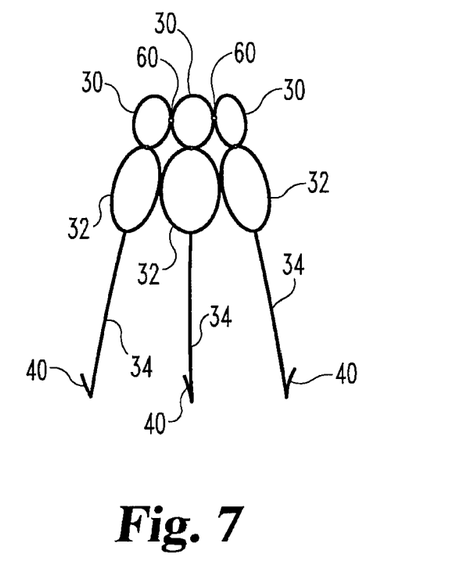
FIG. 7 is a side view of the embodiment of FIG. 6 with further connections.

In other embodiments, segment 22 can be made by providing a sheet of Nitinol or other appropriate material, and cutting it (e.g. by laser or other precision-cutting method) to provide loops 30 and 32 with extension 34 and at least prong 40. If a cannula of material is provided, such cutting methods can be used to remove material from the cannula, making several segments 22 that may already be linked together (e.g. FIGS. 6-8). If necessary, in some embodiments struts 58 can be left or placed between loops 30 of adjacent segments 22 to bend or hold them together. Other methods of making segments 22 or filter 20 can be employed.

In the embodiment shown in FIGS. 1-2, six segments 22 are combined as indicated below to form filter 20. Embodiments using more or fewer segments 22 may be made by substantially similar methods (e.g. individually-formed from thin wire or cut from sheet material, or formed as a whole from a cannula) or in substantially similar configurations. It will be understood that other methods of combining one or more segments 22 may also be used to form filter 20.

In the illustrated embodiment, if segments 22 are made separately, as from separate lengths of wire or cut from a sheet as noted above, then they are attached to each other so that each loop 30 connects on the side to two adjacent loops 30, and each loop 32 connects on the side to two adjacent loops 32. The illustrated embodiments indicate various ways of connecting adjacent loops 30 or adjacent loops 32. For example, in FIGS. 1, 2 and 4 it is shown that adjacent loops 30 and adjacent loops 32 are twisted together, e.g. around each other. In embodiments in which each segment 22 is made of a single wire, the manufacture can be arranged so that as wires are formed into loops for separate segments the wires are intertwined or wrapped around each other to join adjacent loops 30 (or 32). Alternatively, previously individually made segments 22 can be placed adjacent each other and the adjacent portions of loops 30 can be twisted mechanically together, as can the adjacent portions of loops 32. If twisting of the adjacent portions is not desired, other techniques for fastening adjacent loops 30 and adjacent loops 32 with each other can be used. For example, they can be fixed by welding or adhesive, by crimping (alone or with a metal or other sleeve around the portions of the loops), or by placement of a solid bead 60 between or around the adjacent portions of the loops (e.g. FIG. 5).

If such a bead 60 (or other imageable structure) is used, in particular embodiments bead(s) 60 are composed and placed to enhance echogenicity of filter 20. While the segments of filter 20 will have some echogenic quality, bead(s) 60 can provide a clearer or more visible ultrasound image at least due to increased Rayleigh scattering because of their size and profile as compared to loops, extensions, struts or other parts of filter 20. Biologically-suitable polymers or metals are desirable for echogenicity inside the exemplary fluidic environment discussed below. Compared to the thin wire used in embodiments noted above, which may provide discernible but vague or dim imaging, beads 60 provide particular, discrete points that are readily visible under ultrasound. Structural features for disruption or scattering of ultrasound, such as ribbing, indentations, planar surfaces (e.g. circular), or the like, can also be provide on beads 60 to enhance ultrasonic reflectivity. As another example, beads 60 may both increase scattering of ultrasound energy (echogenicity) and be made of a radiopaque material, with examples being beads of gold, platinum, tungsten, tantalum, and similar materials, or radiopaque powder (e.g. barium sulfate) loaded polymers. In such examples, beads 60 provide the ability to place and remove filter 20 under either ultrasound or fluoroscopy visualization. Fluoroscopic visualization may be done from an external source of energy, while ultrasound imaging could be energized from an external source, or from an intravascular ultrasound (IVUS) catheter, which has a transponder and/or receiver located on the tip of an intravascular catheter, or other internal source.

Figure 4:
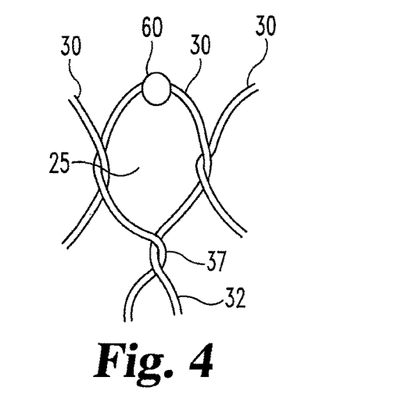
FIG. 4 is a magnified view of a portion of the embodiment shown in FIG. 1.
Figure 5:
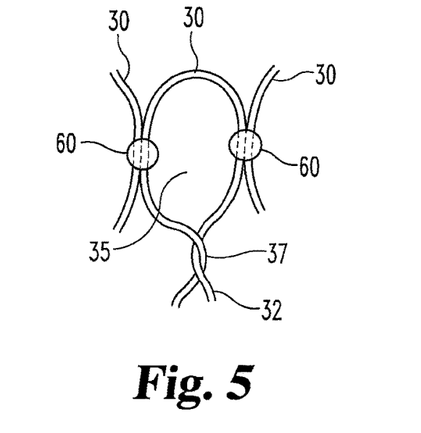
FIG. 5 is a magnified view of a portion of an embodiment generally like the embodiment of FIG. 1.

Placement of beads or surfaces for enhancing echogenicity, regardless of whether they also act to hold segments 22 with respect to each other, provide a number of discrete points for the physician or other professional to visualize or refer to via imaging in placement or removal of filter 20. Such beads may be placed not only at the connections between adjacent loops 30 and/or adjacent loops 32, so that the physician can easily locate those structural positions, but may also be placed in other additional or alternative locations on one or more loops 30, 32 or other parts of filter 20. As seen in the embodiment of FIG. 4, beads 60 are placed at the proximal-most or downstream-most portion of each loop 30, providing essentially a circle of echogenic parts delineating the downstream end of filter 20. Beads 62 (which may identical in form and/or material to beads 60) can be placed at the foot of prongs 40 and/or 42 (e.g. FIG. 3) or at other locations on a filter 20. Beads 62 can provide additional reference information for the physician, e.g. a circle or discrete points indicating the upstream limit of filter 20 in the case of beads 62 located at the respective feet of prongs 40. Beads 62 can also act as a stop for prongs 40, 42, preventing prongs 40, 42 from moving into or through vascular or other tissue beyond a predetermined or desired distance. In the illustrated embodiments, prongs 42 are longer than prongs 40, so that prongs 40, 42 each engage or penetrate the wall of vessel V to approximately the same degree, accounting for the curve of the illustrated embodiment of extension 34.

As indicated at least in FIGS. 1, 2, 4, and 5, loops 30 are connected to adjacent loops 30 at their respective sides, leaving the end-most portion of each loop 30 free. In embodiments in which loops 30 are smaller than loops 32, the connection between the loops 30 and the connection between loops 32 naturally results in loops 30 angling inward toward the longitudinal axis of filter 20. Loops 30 and/or loops 32 may also be initially curved or bent to form the general shape of a dome or cone, e.g. by formation on a dome- or cone-shaped mandrel, by heat-treatment of Nitinol or another superelastic material, or heat-treated to a generally flat or cylindrical shape so that they revert to a curved or domed shape when inserted into the body. With the end portion of each loop 30 free from connection to other loops 30, an unobstructed opening 70 exists between loops 30. Opening 70, surrounded or defined by loops 30, permits blood flow through filter 20 to a greater degree than exists with filters having a central obstruction, as for a retrieval hook. As will be explained further below, opening 70 and the spaces 35, 36 in loops 30 and 32 permit easier removal of filter 20.

Figure 8:
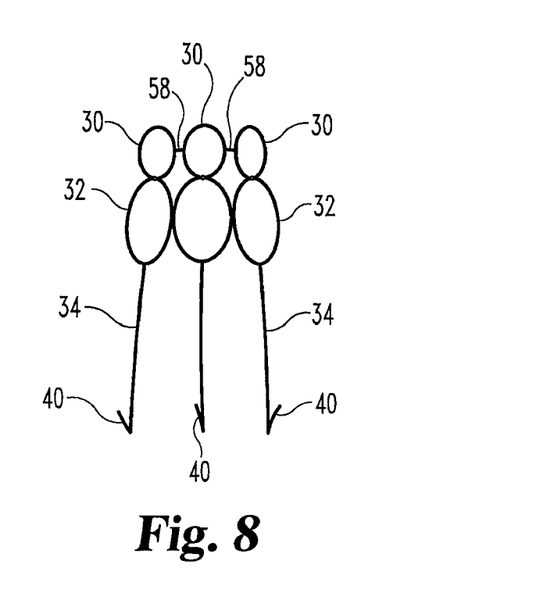
FIG. 8 is a side view of an embodiment like that of FIG. 7, with an alternative set of further connections.
Figure 9:
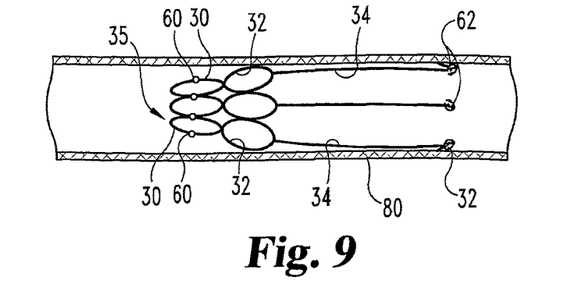
FIG. 9 is a part-cross-sectional view of an embodiment of a vascular filter loaded in an insertion device.

As noted previously, in alternative embodiments some or all of loops 30 and/or loops 32 are not directly twisted, affixed or otherwise connected together, but are connected by a strut 58 (e.g. FIG. 8). Strut 58 allows a greater space to exist between adjacent loops 30 or adjacent loops 32, providing for larger filters. Strut 58 may be made as a part of loops 30 and/or 32, or may be attached later by one or more of the methods noted above for attachment of loops 30 and/or 32 to each other. In particular embodiments, strut 58 may be made of a material different from that of loops 30 and 32, e.g. to provide additional stability to the thin wire of the loops, or to prevent tilting of filter 20. If struts 58 are made of a biodegradeable material, partial or complete dissolution of strut 58 while filter 20 is within a vessel releases the connection between adjacent loops 30 and/or 32. In that case, filter 20 essentially becomes a stent within the blood vessel, and if potential energy is stored in loops 30 and/or 32 (i.e. struts 58 maintain part or all of portion 22 in a more-compressed state than it would otherwise have), then loops 30 and/or 32 can move into engagement with the vessel when released, or when elastic expansive forces overcome one or more of struts 58. It will be understood that a biodegradeable material for struts 58 will be chosen so that they maintain hold on their respective loops 30 or 32 during a period in which filtration of the blood is desired, whether over days, several weeks or a longer period. Biodegradability of struts 58 can eliminate the need to remove filter 20, insofar as it becomes essentially a stent, and will become covered by the vascular endothelium. It will be understood that if more than one strut 58 is used in an embodiment of filter 20, all may be of non-biodegradeable material, all may be of biodegradeable material, or there may be a combination of both kinds of materials.

Insertion and removal of filter 20 into a blood vessel will now be described in certain embodiments. It will be understood that these methods can be used with respect to any of the embodiments of filter 20 described herein, and that variations of such insertion and removal techniques can be used with respect to other parts of the body.

Once the physician or other professional determines that a vascular filter is desired, and where such a filter is to be placed, he or she opens a path to an appropriate part of the circulatory system. As examples, percutaneous access to the femoral artery or vein, carotid artery, jugular vein, or peripheral vessels can be established via a sheath, cannula or similar device. A catheter or sheath 80 having filter 20 packed in a compressed state within its distal end is inserted into the blood vessel and maneuvered to the location at which filter 20 is desired. Filter 20 is preferably compressed radially, so that when it is moved out of the catheter or sheath it expands radially and substantially uniformly. In embodiments in which filter 20 is of a superelastic material, filter 20 can be constructed so that a change in temperature with insertion into the body and the bloodstream causes filter 20 to change state toward resuming an expanded configuration.

Figure 10:
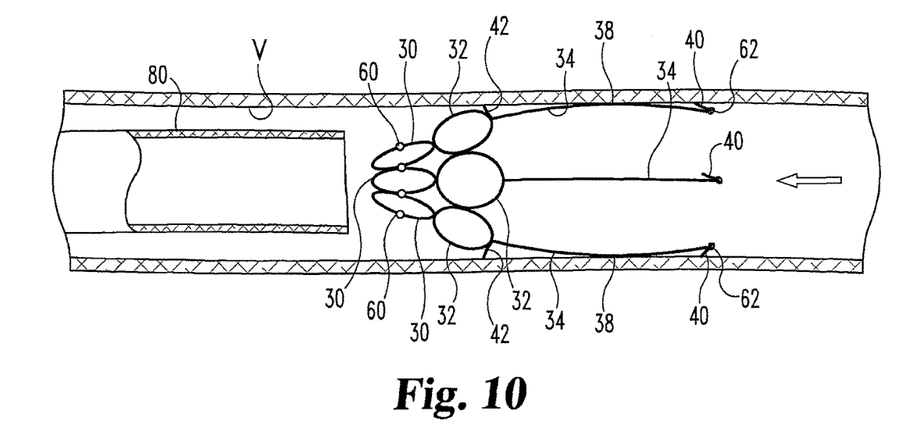
FIG. 10 is a part-cross-sectional view of the embodiment of FIG. 9 with the filter in a vessel.

When catheter 80 loaded with filter 20 is at a desirable location, filter 20 is pushed out of catheter 80, expanding elastically, superelastically or with assistance (e.g. via a balloon or other inflatable member) into contact with the inside of the vessel. In the illustrated embodiment, catheter 80 is advanced against the flow of blood (indicated by the arrow in FIG. 10). In particular embodiments, portions of the extensions 34 (e.g. medial portion 38 and prongs 40, 42) contact the interior of the vessel. In embodiments having prongs 40 and/or 42, the expansion of filter 20 causes prongs 40, 42 to contact and in some embodiments penetrate the vessel wall. The presence of two separated sets of prongs provide independent and complementary anchoring for filter 20. Further, the prongs 40, 42 and extensions 34 of the illustrated embodiment, arranged substantially equidistantly around the circumference of filter 20, are believed to provide collectively enough holding force to allow the thinness of material (e.g. wire, indicated above) used in making filter 20. By increasing the number of prongs and/or extensions, placing them around the circumference, and/or having sets of prongs separated longitudinally, a filter 20 with very thin, flexible and bendable structure is possible. As previously noted, beads 60, 62, if echogenic and placed as noted in the illustrated embodiments, provide the user with an ultrasound view of filter 20, marked by the separated bead sets. Such a view allows the user not only to note the location but also the orientation of filter 20 (e.g. a plane of beads substantially perpendicular to the longitudinal axis of filter 20) with respect to the vessel and its walls. Further, beads 60, 62 placed as illustrated provide a base for prongs 40, 42, limiting the amount of prongs 40, 42 (if any) that extend into a vessel wall.

The expansion of filter 20 into contact with the vessel preferably maintains a minimum amount of extensions 34, and a minimal amount or nothing of loops 30, 32, against the inside of the vessel. As noted above, in embodiments in which extensions 34 have a general outward curve, only the outermost portion 38 of each extension 34, along with prongs 40, 42 (if present), will contact the inside of the vessel. The minimal amount of extensions 34 that contact the vessel means that a minimum amount of extensions 34 can be overgrown by endothelium. Consistent or uniform radial expansion of filter 20 and the even spacing of prongs 40 and/or 42 and separation of prongs 40 from prongs 42 combat the tendency to tilt on insertion that other filters suffer. Observation of orientation of beads 60 and/or 62 allows a determination of whether filter 20 is unacceptably tilted. If so, adjustments to filter 20 can be made with observation of beads 60 and/or 62. Once filter 20 is placed, catheter 80 is removed from the vessel.

With filter 20 inserted into the vessel, blood can flow through filter 20. The presence of central opening 70 between loops 30 (i.e., the lack of a central obstruction or hub) allows better blood flow through filter 20. The material of loops 30 and 32 block the travel of emboli. The conic or domed shape of portion 24 of filter 20 combined with blood flow through filter 20 tend to move emboli toward the forward-middle of filter 20, i.e. toward loops 30. While embolitic material may collect within filter 20, the central opening 70 and/or the openings 35, 36 formed by loops 30, 32 (and/or 32') permit blood to continue to flow. Eventually, embolitic material collected by filter 20 can dissolve back into the bloodstream, or such material can be removed with filter 20.

Figure 11:
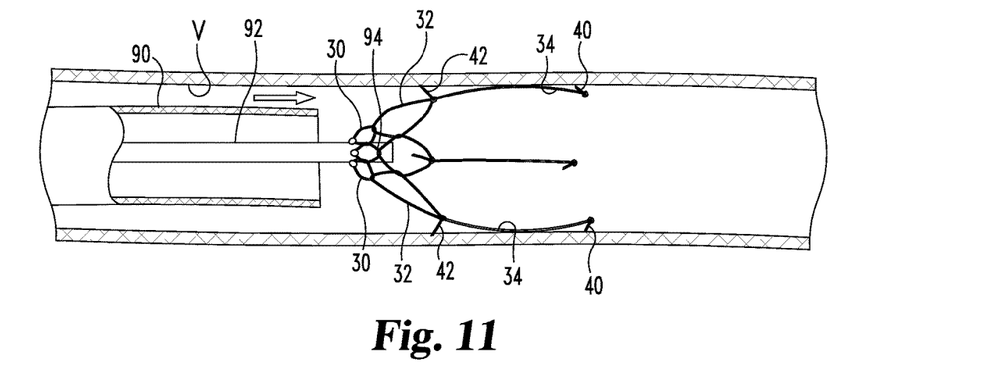
FIG. 11 is a part-cross-sectional view of an embodiment of a vascular filter and structure for moving or removing it.
Figure 12:
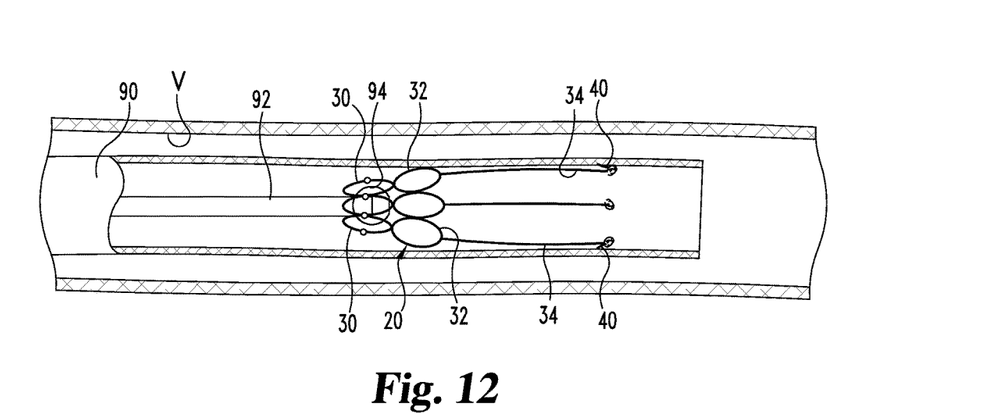
FIG. 12 is a part-cross-sectional view of the structure shown in FIG. 11 with the filter compressed within a device.

At such time as the physician determines that filter 20 is no longer needed, or for another reason decides filter 20 should be moved or removed, access to the vessel and filter 20 is re-established (if access has not been maintained throughout the time that filter 20 has been in the patient). In particular embodiments, a cannula, sheath or other entry device (not shown) is placed in the same or similar location in the patient to allow access along the same or similar path through the vasculature. A catheter or sheath 90 is inserted through the entry device and to a position adjacent distal portion 22 of filter 20 (e.g. generally along the arrow in FIG. 11). From the end of the catheter 90, a secondary catheter 92 with an expandable end 94 is extended through an opening in filter 20. In one example, catheter 90 is inserted through the central opening 70 between loops 30, which is generally easily accessible. In other embodiments catheter 90 can be inserted through the opening 35 or 36 in any of loops 30 or 32. It may be preferred to have catheter 90 inserted through central opening 70, but an advantage of loops 30 and 32 of thin wire is that they present additional openings through which catheter 90 can be extended. The physician or other professional thus need not be so exact or precise in inserting catheter 90, as is generally necessary in connecting with an extraction hook on other types of filters.

With catheter 92 through an opening in filter 20, expandable end 94 is expanded to a diameter greater than that of at least the opening through which catheter 92 extends. In some embodiments, expandable end 94 is or includes a balloon portion, expandable by fluid (liquid or gas). In other embodiments, expandable end 94 could include a spring, a superelastic structure or other piece that can expand to a size that prevents withdrawal of catheter 92 from within filter 20. Catheter 92 can be used to pull filter 20, i.e., by pulling catheter 90 and expandable end 94, expandable end 94 is forced against the material of filter 20 to pull filter 20 along. The thinness of the wire makes filter 20 very flexible, so that when filter 20 is pulled by its portion 24, the prongs 40, 42 pulls on tissue to a lesser extent or not at all. Rather, the interference from the tissue can cause the prongs 40, 42 to pivot away from the tissue, bending the extension 34 (e.g. along curved medial portion 38) and/or loops 32 or other parts of distal portion 22 toward the center of filter 20. While the prongs 40 and/or 42 contact the vessel during the pulling, any damage they may do to the inside of the vessel during pulling is minimized because of the flexibility of the thin material, which allows extension 34 and or prongs 40, 42 to bend rather than forcing them into the tissue. As loops 30 and/or 32 are forced into sheath 90, extensions 34 flex toward the longitudinal axis, further moving prongs 40 and/or 42 away from the wall of the vessel. Filter 20 can in this way be pulled to an exit port, or can be pulled into sheath 90 for removal. In either case, if necessary filter 20 can radially compress on entering the sheath or port.

Alternatively, expandable end 94 can be used as a backstop or buttress to hold filter 20 as sheath 90 is forced over it. Rather than using secondary catheter 92 to pull filter 20 through the vessel any significant distance, expandable end 94 is expanded and moved into contact with or adjacent to the inner surface(s) of filter 20 (i.e., in contact with or adjacent loops 30 and/or 32). With catheter 92 so positioned, sheath 90 can be moved (e.g. along the arrow in FIG. 11) into contact with and over distal portion 22 of filter 20. By holding catheter 92 and its expandable end 94 steady, filter 20 is blocked from movement as sheath 90 pushes against it. Pushing sheath 90 forward thus causes radial compression of filter 20 as it enters sheath 90.

Figure 13:
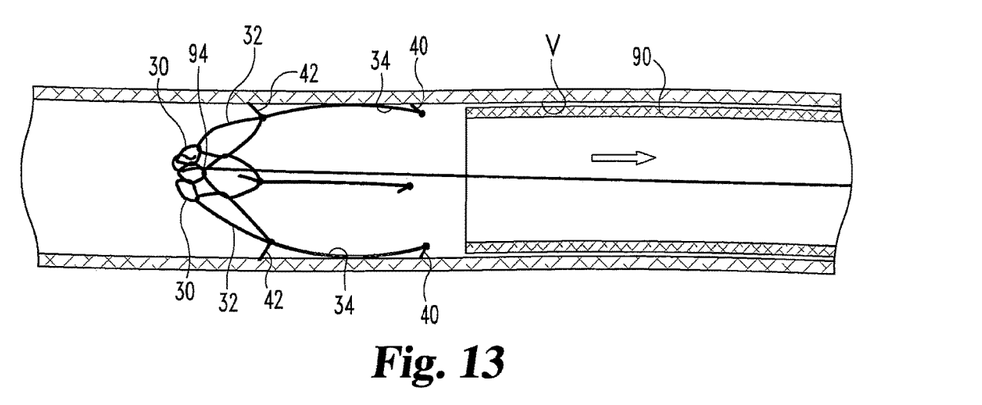
FIG. 13 is a part-cross-sectional view of alternative structure and method of moving or removing a vascular filter.

It will also be understood that sheath 90 can be advanced from upstream (FIG. 13, e.g. opposite to the view of FIG. 11) where indicated or desired, so that sheath 90 is abutting or adjacent to extensions 34 (and prongs 40, if present). Catheter 92 and its expandable end 94 are moved through opening 70 or another opening in filter 20, and end 94 is expanded. Using end 94 as a puller or backstop, as indicated above, filter 20 is forced into sheath 90 led by extensions 34. In embodiments having prongs 40 that form acute angles at their connection at a distal or end portion of extension 34, prongs 40 provide a wedging action when sheath 90 is forced against them. As portion 24 is compressed, the compression causes inward movement or pivoting of each segment 22, resulting in extensions 34 (and prongs 40, 42, if present) moving away from the vessel wall. This method thus reduces risk of damage to the inside of the vessel from withdrawal of filter 20, since the disengagement of filter 20 from the vessel moves the parts of filter 20 inward, directly away from the vessel wall, rather than along the vessel wall.

When filter 20 (or portions of it that may damage the vessel) is within sheath 90, sheath 90 is removed from the body. A new filter 20 (or another type of device, such as a stent) may be placed at the same or a similar location after the removal of the previous filter 20, if desired.

It will also be seen that rather than catheter 92 with expandable end 94, a hook 96 or other gripping or holding device could be passed through sheath 90 and connected to any one or more of loops 30, 32. With hook 96 or other device connected to filter 20, pulling of filter 20 as described above, or holding of filter 20 while sheath 90 is passed over it as described above, can be performed. It is believed that embodiments using expandable end 94 may be more advantageous, at least insofar as the potential for damage to a vessel is lessened with expandable end 94 over a hook (e.g. 96) that may contact the vessel. Nevertheless, embodiments of hooks or other gripping devices can be used to assist in removing filter 20.

In particular embodiments, filter 20 is sufficiently flexible to be everted into sheath 90. Thus, when sheath 90 is positioned adjacent prongs 40, pulling hook 96, expandable device 92, 94, or other gripping device does not draw extensions 34 into sheath 90. Rather, pulling such a device engaging filter 20 but instead causes portion 22 to be drawn through itself, within extensions 34 and into sheath 90. Filter 20 is effectively turned inside out, with portion 22 leading the way into sheath 90.

In the discussion above, blood vessels have been used as the principal example of a location for placement of embodiments of filter 20. It will be understood that embodiments of filter 20 can be used in other vessels, organs or body parts where it is desired to allow flow of fluid yet contain solid or semi-solid materials from traveling through such parts unchecked.

Nitinol and other superelastic materials have been cited as particular materials useful in filter 20, as they will provide the ability to resume an unstressed configuration suited to the diameter of a vessel, and will have a flexibility desirable for the compression and flexing described above. Other biocompatible materials could be used for embodiments of filter 20, particularly those for which such flexibility is unnecessary or undesired.

In embodiments in which prongs 40 and/or 42 are provided, prongs 40, 42 anchor filter 20 to the vessel, by themselves or in conjunction with spring force applied by extensions 34. These features are believed to hold filter 20 within the vessel better than merely relying on firmness of a filter's wires, as in other devices. As indicated above, loops 30, 32 may be thought of as a "downstream" or distal portion of filter 20, while extensions 34 may be thought of as an "upstream" or proximal portion of filter 20.

The exemplary discussion above discussed capture, removal and/or repositioning of embodiments of filter 20 using a balloon catheter as an expandable or inflatable member. It is noted that other types of devices can be used as such an expandable or inflatable member. For example, a malecot catheter with its expandable side pieces or wings (which normally anchor or stabilize the catheter in a duct or organ) may be used, with the expandable wings performing pulling or bolstering tasks described above with respect to a balloon. Moreover, the expandable member need not be a catheter at all, but instead a mechanical or other type of expanding device, such as a forceps or grasper tool, or an expandable basket akin to those used for containing kidney or other bodily stones.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected. It will be understood that features or attributes noted with respect to a specific embodiment may be used or incorporated into other embodiments of the structures and methods disclosed.

What is claimed is:

1. A vascular filter system, comprising
a vascular filter made of a plurality of wire segments,
each wire segment of said plurality of wire segments including
at least one first unobstructed elliptic loop having a center, a distal part, and an opposed proximal part,
a second unobstructed elliptic loop, larger than the at least one first unobstructed elliptic loop, having a center and directly connected to the distal part of the at least one first unobstructed elliptic loop, and
a curvilinear extension formed as a distal end of each wire segment extending longitudinally in a distal direction from the second unobstructed elliptic loop, wherein said second unobstructed elliptic loop fixed to said at least one first unobstructed elliptic loop at a location along a longitudinal line connecting said centers of said at least one first unobstructed loop and said second unobstructed loop,
said second unobstructed elliptic loop is directly connected to the distal part of the at least one first unobstructed elliptic loop, and the distal part of the at least one unobstructed elliptic loop is radially further outwards from a central longitudinal axis of the vascular filter than is the opposed proximal part of the at least one unobstructed elliptic loop,
each said at least one first unobstructed elliptic loop of each wire segment being connected to one or more adjacent first unobstructed elliptic loops of adjacent wire segments of the plurality of wire segments so that the opposed proximal parts of said first unobstructed elliptic loops of the plurality of wire segments frame an opening between them,
each said second unobstructed elliptic loop of each wire segment being connected to one or more adjacent second unobstructed elliptic loops of adjacent wire segments; and,
an expandable member extendable at least through said opening, said expandable member having a first contracted state in which said expandable member can be moved through said opening, and a second expanded state in which said expandable member cannot be moved through said opening, wherein expanding said expandable member within said vascular filter allows said expandable member to engage said vascular filter to pull or buttress said vascular filter in a blood vessel.

2. The system of claim 1, further comprising a tubular member adapted to be inserted into a vascular system, said tubular member having a lumen, wherein said expandable member is extendable from said tubular member, and wherein said lumen is adapted to accommodate said vascular filter moved into it from a position in a blood vessel.

3. The system of claim 1, wherein said plurality of wire segments are substantially identical.

4. The system of claim 1, wherein at least a first of said first unobstructed elliptic loops of said plurality of wire segments is connected to a second of said first unobstructed elliptic loops of said plurality of wire segments by twisting respective portions of said first and second of said first unobstructed elliptic loops together.

5. The system of claim 1, wherein at least a first of said first unobstructed elliptic loops of said plurality of wire segments is connected to a second of said first unobstructed elliptic loops of said plurality of wire segments by a holding piece that holds respective portions of said first and second of said first unobstructed elliptic loops with respect to each other.

6. The system of claim 5, wherein said holding piece is an echogenic bead.

7. The system of claim 1 further comprising a plurality of visualizable beads, wherein each said at least one first unobstructed elliptic loop is linked to said one or more adjacent first unobstructed elliptic loops by one of said plurality of visualizable beads, said plurality of visualizable beads lying substantially in a single plane that is approximately perpendicular to the central longitudinal axis of said vascular filter.

8. The system of claim 1, wherein each said wire segment of said plurality of wire segments includes first and second prongs placed generally at opposite ends of the curvilinear extension of each said wire segment, and wherein said vascular filter is configured so that on placement in a vessel at most a portion of said curvilinear extensions and a portion of each of said first and second prongs contact the vessel.

9. A vascular filter system, comprising:
a vascular filter having a plurality of wire segments joined together,
each wire segment of said plurality of wire segments including
a first unobstructed elliptic loop having a center, a distal part, and an opposed proximal part,
a second unobstructed elliptic loop larger than the first unobstructed elliptic loop having a center and directly connected to the distal part of the first unobstructed elliptic loop, and fixed to said first unobstructed elliptic loop at a location along a longitudinal line connecting said centers of said loops, and
an extension fixed to said second unobstructed elliptic loop and extending generally away from said first unobstructed elliptic loop,
wherein said first unobstructed elliptic loop of each wire segment is joined to at least one other of said first unobstructed elliptic loops of an adjacent wire segment of the plurality of wire segments, and said second unobstructed elliptic loop of each wire segment is joined to at least one other of said second unobstructed elliptic loops of an adjacent wire segment, and the distal part of the first unobstructed elliptic loop is radially outward from a central longitudinal axis of the vascular filter than is the opposed proximal part of the first unobstructed elliptic loop,
and wherein said first unobstructed elliptic loops of the plurality of wire segments when joined together frame a central longitudinal opening that is surrounded by the opposed proximal parts of said first unobstructed elliptic loops of the plurality of wire segments, and
wherein said extensions are curved so that their respective internally-facing portions are concave,
an expandable member extendable at least through said central longitudinal opening, said expandable member having a first contracted state in which said expandable member can be moved through said central longitudinal opening, and a second expanded state in which said expandable member cannot be moved through said central longitudinal opening, wherein expanding said expandable member within said vascular filter allows said expandable member to engage said vascular filter to pull or buttress said vascular filter in a blood vessel.

10. The system of claim 9, wherein at least one of said plurality of wire segments includes a first prong located at or adjacent to the point where the extension and second unobstructed elliptic loop of said wire segment are fixed together, and a second prong located on said extension distal from said second unobstructed elliptic loop.

11. The system of claim 10, wherein said vascular filter is configured so that when properly placed in a vessel only a portion of said extension and a portion of each of said first and second prongs contact the vessel.

12. The system of claim 10, wherein said at least one of said wire segments of the plurality of wire segments includes a first bead contacting said first prong and said extension and said second unobstructed elliptic loop, and a second bead contacting said second prong and said extension, said first and second beads acting as a limit on a distance said first and second prongs can be inserted into tissue.

13. The system of claim 10, wherein said first prong and said second prong are substantially parallel to each other.

14. The system of claim 10, wherein said second prong forms an acute angle with respect to said extension.

15. The system of claim 9, wherein said vascular filter includes at least one bead contacting two adjacent first unobstructed elliptic loops of said first unobstructed elliptic loops of the plurality of wire segments.

16. The system of claim 15, wherein said at least one bread is echogenic.

17. The system of claim 16, wherein said at least one bead includes a series of beads each contacting two adjacent first unobstructed elliptic loops of said first unobstructed elliptic loops of the plurality of wire segments, said series of beads being generally in a plane.

18. The system of claim 9, wherein said vascular filter includes at least one echogenic bead on a portion of one of said first unobstructed elliptic loops of the plurality of wire segments adjacent to said central longitudinal opening.

19. The system of claim 9, further comprising a tube through which said expandable member extends and from which said expandable member is moved through said vascular filter, said tube sized and configured to permit placing said expandable member and said vascular filter into said tube so as to remove said vascular filter from said blood vessel.

20. The system of claim 9, wherein each said extension of each wire segment extends from said second unobstructed elliptic loop of each respective wire segment to a distal end, and wherein each said extension has an outermost external surface that lies between said second unobstructed elliptic loop and said distal end, wherein the outermost external surface is adapted to engage the inside of a vessel while portions of said extension more proximal or more distal of the outermost external surface have separation from the inside of the vessel.

* * * * *

UNITED STATES PATENT AND TRADEMARK OFFICE
CERTIFICATE OF CORRECTION

PATENT NO. : 9,675,438 B2  
APPLICATION NO. : 13/901132  
DATED : June 13, 2017  
INVENTOR(S) : Charles W. Agnew Page 1 of 1

It is certified that error appears in the above-identified patent and that said Letters Patent is hereby corrected as shown below:

Column 15, Line 14, Claim 7, please correct "visulalizable" to --visualizable--.
Column 16, Line 34, Claim 16, please correct "bread" to --bead--.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*